United States Patent [19]

Barlow

[11] Patent Number: 5,768,712
[45] Date of Patent: Jun. 23, 1998

[54] SPORTSWEAR UNDERGARMENT FOR RESIDUAL LEG

[76] Inventor: Blake Barlow, 3011 N. Hudson Ave., Oklahoma City, Okla. 73103

[21] Appl. No.: 855,292

[22] Filed: May 13, 1997

[51] Int. Cl.$^6$ ................................ A41B 9/02; A61F 2/78
[52] U.S. Cl. ...................... 2/400; 2/404; 2/238; 623/36
[58] Field of Search .............................. 623/33, 36, 35, 623/27, 31, 32; 2/227, 228, 238, 270, 72, 83, 400, 404, 22, 401, 402, 407, 239, 240; 602/62, 63; 604/345

[56] References Cited

U.S. PATENT DOCUMENTS

| 1,285,507 | 11/1918 | Waterman | 623/33 |
|---|---|---|---|
| 1,341,317 | 5/1920 | Hanna | 2/83 |
| 1,461,987 | 7/1923 | Smith . | |
| 2,743,451 | 5/1956 | Meyers | 2/83 |
| 3,032,035 | 5/1962 | Dempsey | 602/62 |
| 3,201,800 | 8/1965 | McHugh | 2/83 |
| 4,635,626 | 1/1987 | Lerman | 128/165 |
| 4,644,946 | 2/1987 | Cremona-Bonato | 602/63 |
| 4,840,635 | 6/1989 | Smith et al. | 623/36 |
| 4,870,708 | 10/1989 | Staley | 2/404 |
| 4,870,958 | 10/1989 | Webster | 2/404 |
| 5,131,100 | 7/1992 | Atwater et al. | 2/404 |
| 5,191,659 | 3/1993 | Backus | 2/228 |
| 5,210,882 | 5/1993 | Moretz et al. | 2/404 |
| 5,376,130 | 12/1994 | Courtney | 623/33 |
| 5,535,453 | 7/1996 | Howard | 2/269 |
| 5,592,693 | 1/1997 | Jensen et al. | 2/115 |
| 5,603,122 | 2/1997 | Kania | 2/239 |

Primary Examiner—Amy B. Vanatta
Attorney, Agent, or Firm—R. William Graham

[57] ABSTRACT

The sportswear undergarment for a residual leg includes an expansible waist band for encircling a waist of a wearer, a fabric seat portion connected to the waist band, a fabric abdomen portion connected to the seat portion and waist band in a manner such that the seat and abdomen portions substantially enclose the seat and abdomen of the wearer while defining a pair of oppositely disposed open surfaces, a first fabric leg portion connected to one part of the open surfaces and extending in an encircling manner therefrom to a predetermined region about one thigh and a second fabric leg portion connected to another of the open surfaces and extending in an encircling manner therefrom to a predetermined region about another thigh, wherein at least one of the leg portions further includes an enclosed end configured to conformingly receive a residual leg portion of an amputee.

3 Claims, 4 Drawing Sheets

SPORTSWEAR UNDERGARMENT FOR RESIDUAL LEG

BACKGROUND OF THE INVENTION

1. Field of the Invention

The present invention relates to undergarments for amputees. More particularly, the invention relates to a sportswear undergarment for an amputee having a residual leg.

2. Related Art

There exist various types of undergarments and clothing for amputees. For example U.S. Pat. No. 5,592,693 discloses a shirt which can be worn by an amputee to protect the residual limbs from unwanted friction and rubbing.

U.S. Pat. Nos. 5,603,122 and 4,840,635 disclose a form fit sock for use on a residual leg portion. Socks typically require a separate support means (such as an additional elastic band) to maintain the sock in a desired place. This presents the wearer with undue discomfort when wearing additional underwear components.

Because the residual leg is subjected to pressures incurred during walking or exercising using a prosthetic device, the residual leg is subject to increased swelling and irritation. One focus of the industry has centered on designing socks to fit various shaped residual legs and improve wearability with a prosthetic device.

A common problem which occurs is the bunching of sock material at a lower end of the residual leg which inhibits the material and leg ability to breath. Thus, the industry has specially designed a sock (e.g., an elastic sock) which conforms to the residual leg. While the problem thus far has been addressed by specially designed fabrics to conform to and maintain their position on the residual leg, the elastic material restricts circulation in the residual leg.

Even with the improvements which have been made in the art, there remains a need to improve upon the art. Particularly, there is a need to provide a more versatile lower body undergarment which is more comfortable to the wearer. There is also a need to improve sportswear undergarments for use on residual leg portions of an amputee. It is also desired to improve lower undergarments for use with prosthetic devices.

BRIEF SUMMARY OF THE INVENTION

It is an object to improve lower body undergarments for use with a residual leg of an amputee.

It is another object to improve lower undergarments for use with prosthetic leg devices.

It is still another object to provide a sportswear undergarment for an amputee having a residual leg.

Another object is to provide a lower body undergarment for an amputee which includes components which can be readily produced in a manner to provide a relatively custom fit to the wearer.

Accordingly, the present invention is directed to a sportswear undergarment for an amputee having a residual leg. The undergarment includes an expansible waist band for encircling a waist of a wearer, a fabric seat portion connected to the waist band and a fabric abdomen portion connected to the seat portion and waist band in a manner such that the seat portion and abdomen portion substantially enclose the seat and abdomen while defining a pair of oppositely disposed open surfaces. A first fabric leg portion connects to one of the open surfaces and extends in an encircling manner therefrom to a predetermined region about one thigh. A second fabric leg portion connects to another of the open surfaces and extends in an encircling manner therefrom to a predetermined region about another thigh, wherein at least one of the leg portions further includes an enclosed end configured to conformingly receive a residual leg portion of an amputee. The invention may also include two enclosed end portions in the case of an amputee having two residual legs.

Other objects and advantages will be readily apparent to those skilled in the art upon viewing the drawings and reading the detailed description hereafter.

DETAILED DESCRIPTION OF THE INVENTION

Figure 1:
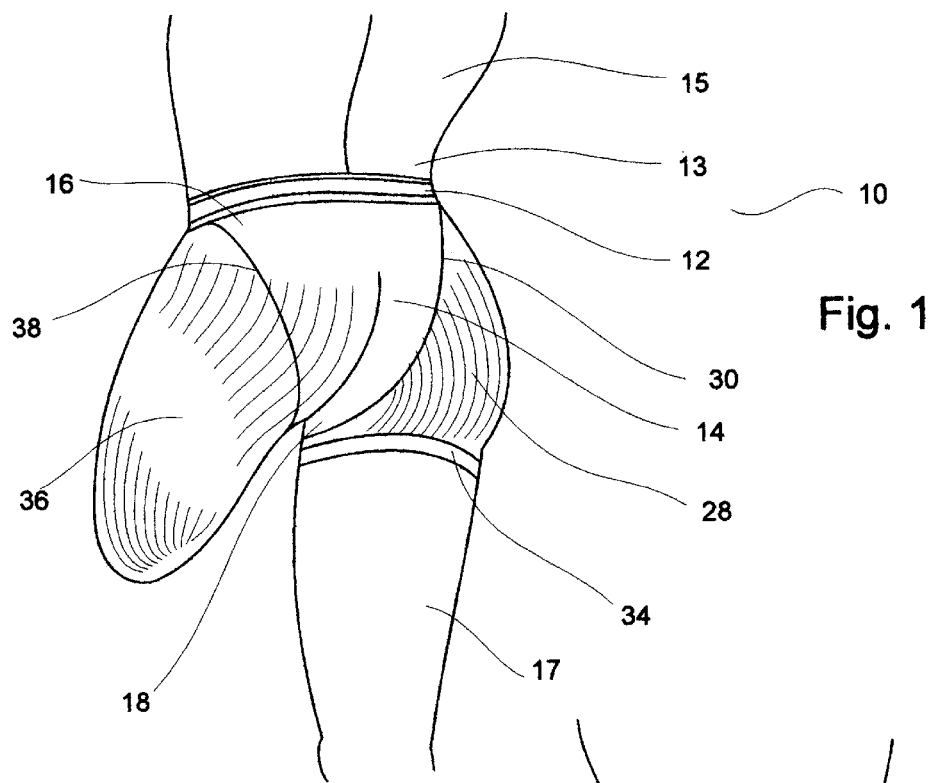
FIG. 1 is a rear fragmentary view of a human amputee illustrating the present invention.
Figure 2:
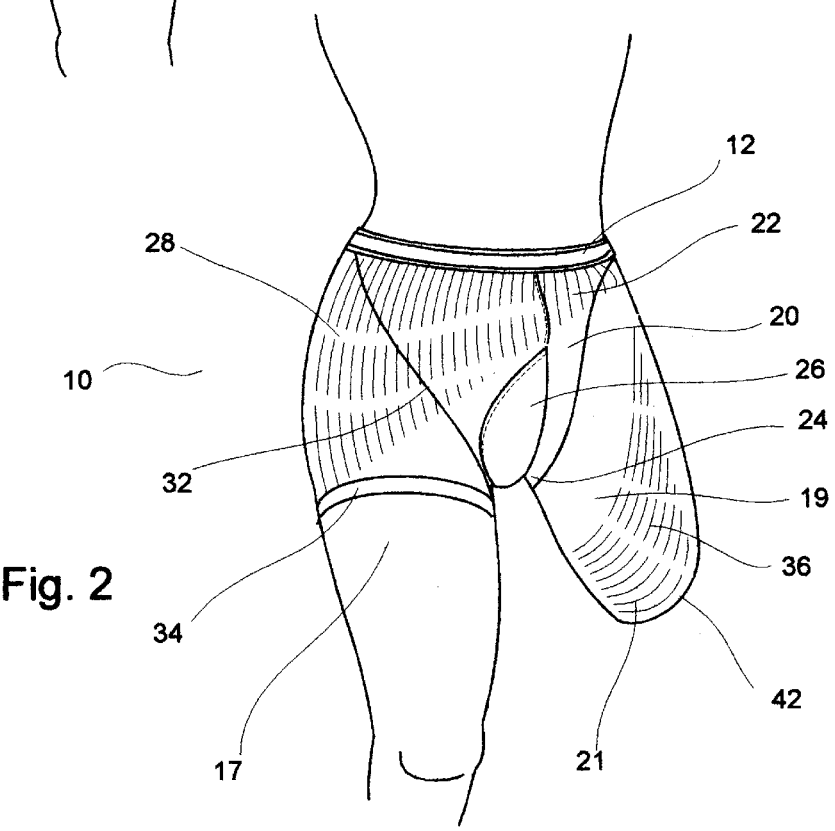
FIG. 2 is a front fragmentary view of a human amputee illustrating the present invention as shown in FIG. 1.

Referring now to the drawings, the sportswear undergarment of present invention is generally designated by the numeral 10, as seen in FIGS. 1 and 2. The sportswear undergarment 10 generally is made of a fabric material known to those skilled in the art. For example, the fabric material can be cotton, wool, synthetic, fleece, linen, polyester, knit or blends thereof Here, the general nature of the fabric need not be so elastic as to be self-supporting and hence restrict circulation. Rather, the material can be made to conform to the seat, abdomen and leg, yet in a more relaxed fit and still accomplish the objectives herein.

The sportswear undergarment 10 includes an expansible waist band 12 for encircling a waist 13 of a wearer 15. The waist band 12 is preferably of an elastic material having a fabric covering of a material described above.

A fabric seat portion 14 is connected to the waist band 12 and is generally tapered with a wider end 16 connected adjacent the waist band 12 and extending to a narrower end 18 adjacent a crotch area of the wearer 15. An abdomen portion 20 is likewise formed in a tapered manner having a wider portion 22 connected adjacent the waist band 12 and extends toward the crotch area of the wearer 15 terminating in a narrower end 24. The ends 18 and 24 are connected, either via stitching or are integrally formed into one piece in the crotch area. Additionally, the abdomen portion 20 includes an overlapping fly portion 26.

The seat portion 14 has an edge 30 and the abdomen portion 20 has an edge portion 32 which join to form a generally circular open surface 31. The leg potion 28 connects to the open surface 31 in a stitched manner, for example and extends in an encircling manner therefrom to a predetermined region 17, preferably a mid-region, about one thigh. The leg portion 28 is preferably made of a like material to that of the seat portion 14 and abdomen portion 20. A terminal end 34 of the leg portion 28 includes a generally circular elastic member 34 to aid in retaining the sportswear undergarment 10 in a desired position.

The seat portion 14 has an edge 38 and the abdomen portion 20 has an edge portion 40 which join to form a generally circular open surface 41. The leg potion 36 connects to the open surface in a stitched manner, for example, and extends in an encircling manner therefrom to a predetermined region 19, preferably a mid-region, about one thigh and further includes an enclosed end 42 configured to conformingly receive a residual leg portion 21 of the wearer 15. The leg portion 36 is preferably made of a like material to that of the seat portion 14 and abdomen portion 20 described above.

Figure 3:
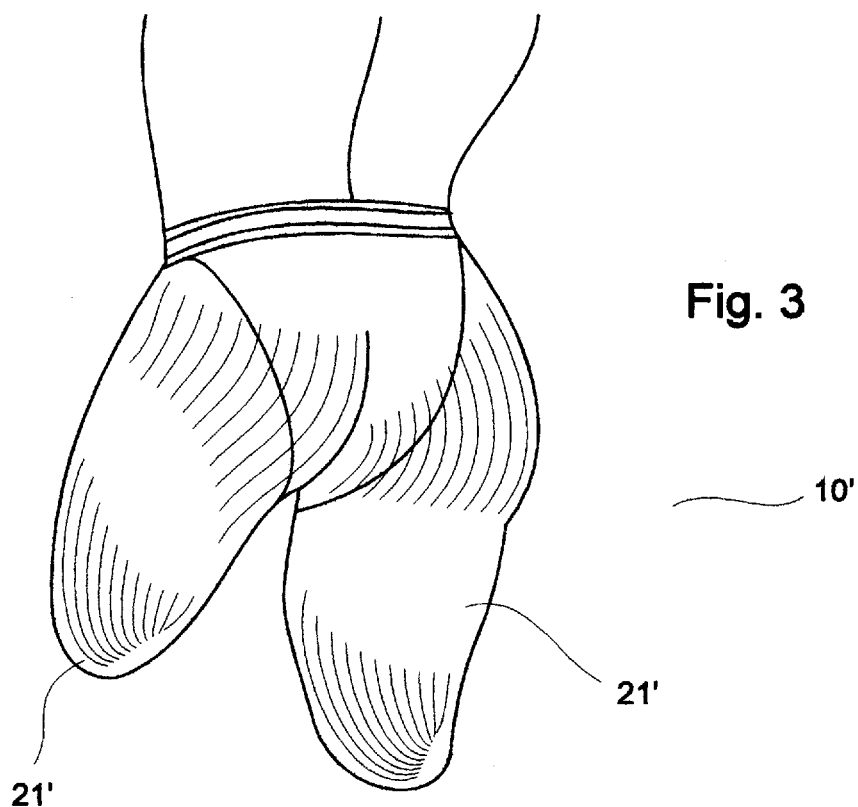
FIG. 3 is a rear fragmentary view of a human amputee illustrating another embodiment of the present invention.
Figure 4:
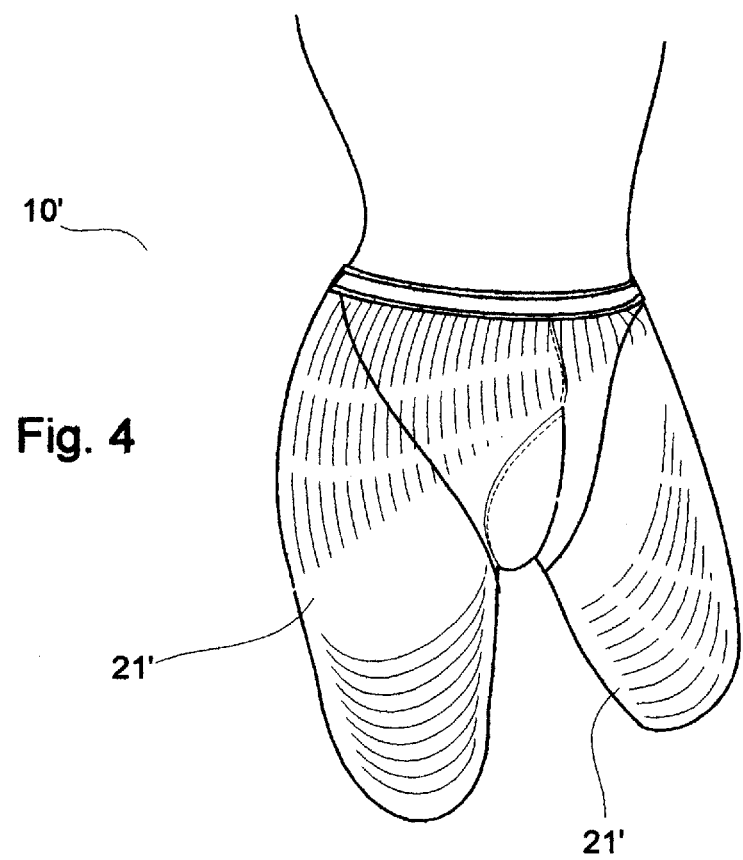
FIG. 4 is a front fragmentary view of a human amputee illustrating the embodiment shown in FIG. 3.
Figure 5:
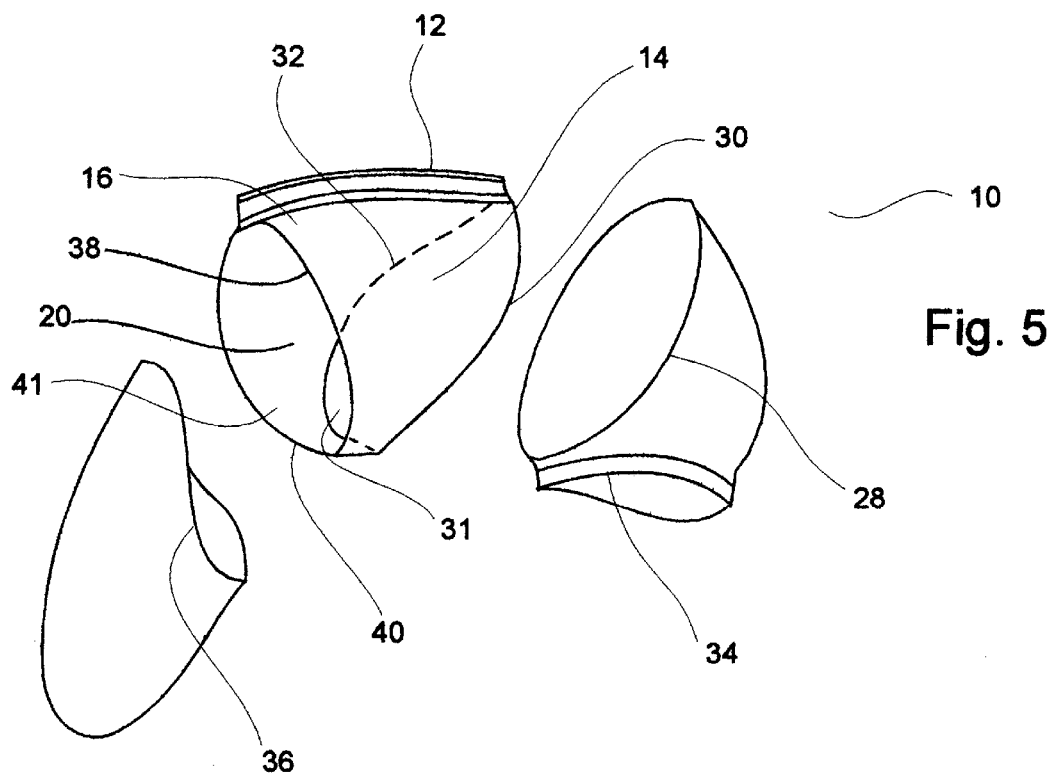
FIG. 5 is an exploded view of the present invention as illustrated in FIG. 1.
Figure 6:
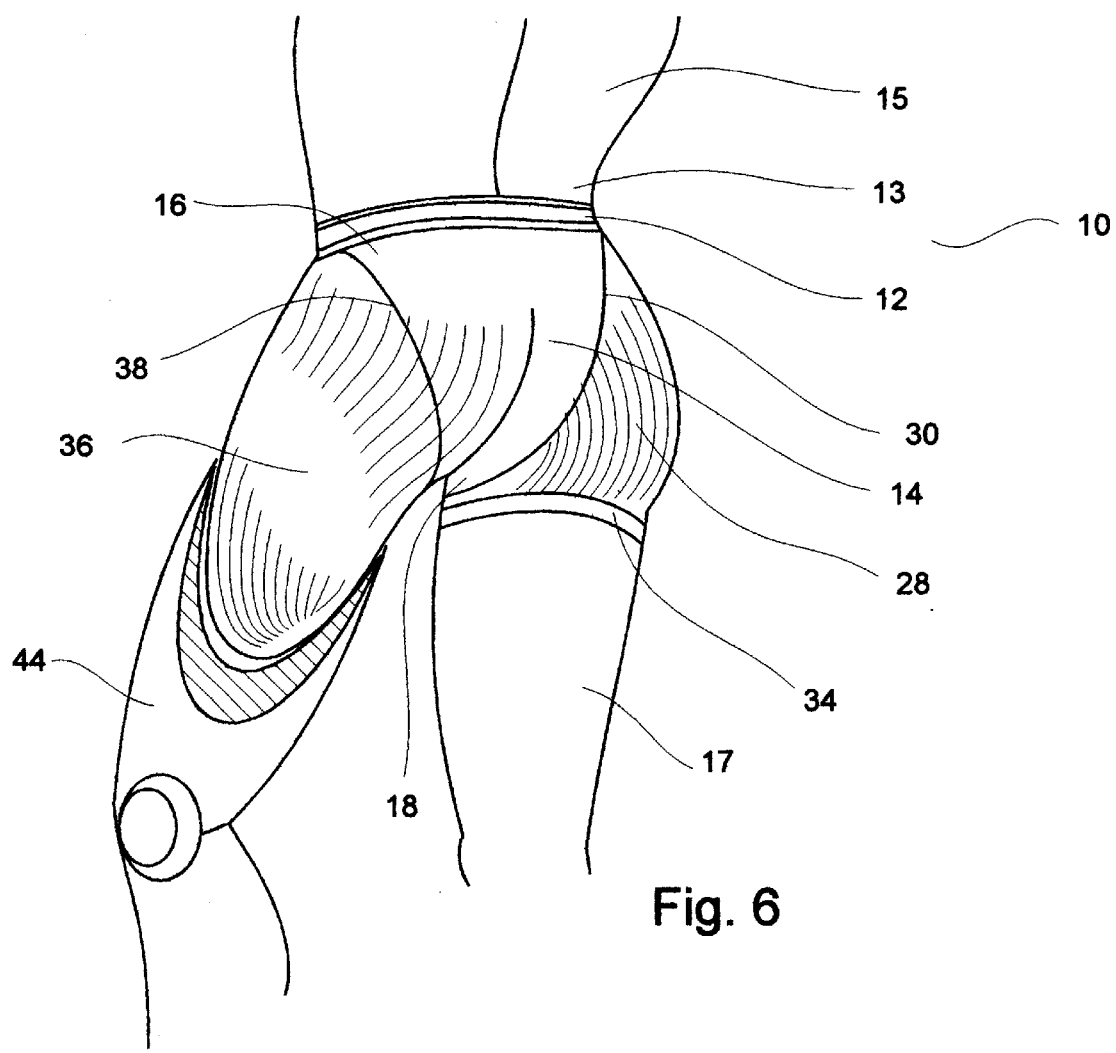
FIG. 6 is a rear fragmentary view of a human amputee illustrating the sportswear undergarment with cross-sectional view the prosthesis of the present invention.

FIGS. 3 and 4 depict another embodiment of the invention which shows a sportswear undergarment 10'. Here, there are shown two residual leg portions 21'. The sportswear undergarment 10' is formed in a similar manner to that described above with the exceptions that there are two leg portions 36' formed in a similar manner to leg portion 36 described above.

The construction of the sportswear undergarments 10 and 10' of the present invention provide the wearer with several advantages over the related art. Here, the invention provides for a single unitary lower body undergarment. This does away with the combined wearing of underwear and an additional sock which required a separate support means. The sportswear undergarment 10 and 10' present the wearer with a balanced feel and does away with the need for an independent sock.

It also believed that the unitary structure of the present invention will permit use of more relaxed fabrics while aiding in preventing bunching of the material adjacent the lower portion of the residual leg. Thus, there is reduced irritation of the leg by virtue of the residual leg portion being part of an entire undergarment with relatively equal distribution of forces on the material being maintained on both legs. In a physically active environment, the wearer will tend to stretch and pull on the sportswear undergarment more equally from both sides and hence provide the wearer with less bunching of fabric adjacent the prosthetic device 44 and increase breathableness adjacent the residual leg.

The above described embodiments are set forth by way of example and are not for the purpose of limiting the present invention. It will be readily apparent to those skilled in the art that obvious modifications, derivations and variations can be made to the embodiments without departing from the scope of the invention. Accordingly, the claims appended hereto should be read in their full scope including any such modifications, derivations and variations.

What is claimed is:

1. A sportswear undergarment and prosthetic leg device for a residual leg of an amputee, which includes:

sportswear undergarment for a residual leg of the amputee having at least one leg surgically severed to terminate in a residual leg, the sportwear undergarment constructed substantially of a single unitary fabric having an expansible waist band encircling a waist of the amputee, a fabric seat portion connected to the waist band, a fabric abdomen portion connected to said seat portion and said waist band in a manner such that said seat portion and said abdomen portion substantially enclose a seat and an abdomen of the amputee while defining a pair of generally oppositely disposed open surfaces;

a first leg portion connected to one of said open surfaces and extending in an encircling manner therefrom to a predetermined region about one thigh of the amputee and includes an enclosed end configured to conformingly receive the residual leg portion of the amputee and seat in the prosthetic leg device, a second leg portion connected to another of said open surfaces and extending in an encircling manner therefrom to a predetermined region about another thigh of the amputee sufficient to aid in the retention of said sportswear undergarment from undesirable bunching and displacement of said undergarment during use.

2. The sportswear undergarment of claim 1, wherein said second of said leg portions has an elastic band member connected at a terminal end thereof in a manner to aid in retention thereof.

3. The sportswear undergarment of claim 1, wherein each of said leg portions further includes an enclosed end configured to conformingly receive a residual leg portion of the amputee.

\* \* \* \* \*